United States Patent [19]

Whitten

[11] Patent Number: 4,762,790

[45] Date of Patent: Aug. 9, 1988

[54] PROCESS FOR MICROPLANT PROPAGATION THROUGH INCREASED MULTIPLE SHOOT FORMATION

[75] Inventor: George H. Whitten, Woodridge, Ill.

[73] Assignee: CPC International Inc., Englewood Cliffs, N.J.

[21] Appl. No.: 823,859

[22] Filed: Jan. 29, 1986

[51] Int. Cl.$^4$ .................. C12N 5/00; C12N 5/02
[52] U.S. Cl. .................. 435/240.45; 435/240.4; 435/240.54
[58] Field of Search ............ 435/240, 241, 240.4, 435/240.45, 240.54

[56] References Cited

U.S. PATENT DOCUMENTS 4,569,914 2/1986 Molnar et al. .

FOREIGN PATENT DOCUMENTS 0098234 1/1984 European Pat. Off. .

OTHER PUBLICATIONS

El-Ashwah et al., 1980, Chem. Abstr. 92: #162149g.
Brown et al., 1985, Biol. Abstr. 81(5): #42176.
Lewis et al., 1983, Biol. Abstr. 76(12): #91132
Mellor et al., 1976, pp. 618-621 In: Plant Cell, Tiss. and Organ Cult., Reinert et al., eds., Springer-Verlag; New York.
Hu et al., 1983, pp. 196-198 In: Handbook of Plant Cell Culture, vol. I, Evans et al., eds., Macmillan; New York.
Murashige, *Ann. Rev. Plant Physiol.*, 25, 135-166 (1974).
Fox et al, *Plant Physiology*, 577-579 (1959).
Shepard, "The Regeneration of Potato Plants from Leaf-Cell Protoplasts", *Scientific American*, 246, No. 5, 112-121 (1982).

*Primary Examiner*—Charles Fularpen
*Assistant Examiner*—David T. Fox

[57] ABSTRACT

A process for increasing the rate of shoot formation in plant propagation by tissue culture. The tissues are cultured on a growth medium which comprises steepwater.

11 Claims, No Drawings

PROCESS FOR MICROPLANT PROPAGATION THROUGH INCREASED MULTIPLE SHOOT FORMATION

FIELD OF THE INVENTION

The present invention relates to a process for the clonal propagation of plants by multiple shoot formation from organ tissue cultures.

BACKGROUND OF THE INVENTION

A number of plants are propagated commercially by the tissue culture method. According to this method selected tissues of the desired plant are grown on a medium which causes multiplication of the tissues. These multiplied tissues are divided and the divisions are grown on other media which cause rapid increase of organs and other structures ultimately giving rise to complete regenerated plants.

The plant regeneration can be achieved from organized cell systems, such as bud, stem segment, shoot tip, meristem, and other organ cultures. Regeneration can also be accomplished using unorganized systems, such as callus and suspension-cultured cells. Since true clones of a plant are most readily obtained from regenerated plants by means of axillary shoots from organized systems, such systems are usually used as the starting material for commercial microplant propagation.

The efficiency of plant propagation by means of multiple shoot formation from organized systems depends on the rapid formation of a number of shoots from the system. The present invention is based on a discovery of a process for increasing the rate at which shoots are produced from the organized systems. Furthermore, the process of this invention greatly enhances the rate of formation of roots and other structures thereby accelerating the rate of formation of complete regenerated plants.

SUMMARY OF THE INVENTION

In accordance with this invention, there is provided a process for increasing the rate of shoot formation in plant propagation by tissue culture comprising culturing tissues on a growth medium which comprises steepwater.

Further provided, in accordance with this invention, is a process for the propagation of a potato plant which comprises the steps of:

culturing shoots of the potato plant on nodal propagation media which comprises steepwater until the shoots produce multiple nodes;

cutting the cultured material into sections, each of said sections containing a single node; and subculturing each section containing a single node on nodal propagation media which comprises steepwater to produce multiple copies of the potato plant.

DETAILED DESCRIPTION OF THE INVENTION

General methods for plant propagation through tissue cultures are well known and have been extensively described in the literature. See, for example, the extensive review entitled "Plant Propagation Through Tissue Cultures" by T. Murashige, *Ann. Rev. Plant Physiol.*, 25, 135–166 (1974). Description of the conditions used for propagation of various plants including media, temperature, light conditions, and types of cultures used are referred to therein in detail.

The corn wet-milling process is also well known and has been extensively described in the literature. See, for example, the chapter entitled "Starch" by R. L. Whistler and J. R. Daniel, beginning on page 492 of Vol. 21 of *Kirk-Othmer: Encyclopedia of Chemical Technology*, Third Edition, John Wiley & Sons, Inc., New York (1983). Other grains, such as wheat and sorghum, may also be subjected to the wet-milling process.

When corn is subjected to the wet-milling process, the grain is first soaked in warm water which usually contains a small amount of sulfur dioxide. When wheat is subjected to the wet-milling process, sulfur dioxide is not ordinarily added to the water, since it destroys the vitality of the wheat gluten. After the grain is removed, the residual aqueous solution containing various substances which have leached out of the grain is often referred to as steepwater. As used herein, the term "steepwater" will also be used to include the solution which has been concentrated by evaporation and to the steepwater solids which remain when evaporation is carried out to completion.

In the practice of this invention, the steepwater is mixed with the nutrient media on which the tissue cultures are grown. From about 0.05 g to about 5 g of steepwater on a dry solids basis is added per liter of medium. This corresponds to a medium containing from about 0.01% to about 1% of commercial steepwater, since commercial steepwater, sometimes referred to as corn steep liquor, is about 50% water. A preferred concentration of steepwater in the medium is from about 0.5 g to about 5 g of steepwater on a dry solids basis per liter of medium.

A particularly desirable steepwater to be used in the process of this invention is obtained by subjecting commercial steepwater to ultrafiltration. A suitable product is the retentate obtained when the material is processed through a 1000-molecular weight cutoff membrane at a 9:1 permeate to retentate ratio.

Plants which can be propagated in accordance with this invention include houseplants, decorative and ornamental shrubs and trees, and agricultural crops and trees, including but not limited to: orchids, ferns, chrysanthemums, potatoes, lilies, duckweed, clover, and apple, almond, pine and papaya trees.

The following examples illustrate certain embodiments of the present invention. Unless otherwise stated, all proportions and percentages are provided on the basis of weight.

EXAMPLE 1

Potato shoot cultures were initiated from shoot tips excised from "eyes" of potato tubers. Excised shoot tips, consisting of apical domes accompanied by 4- to 6-leaf primordia, were placed upon shoot initiation media given in Table I. When these cultures had produced 4 to 8 nodes, segments containing individual nodes were separated and subcultured on nodal propagation media. The composition of the nodal propagation media was similar to the shoot initiation media except that the kinetin and indole acetic acid were omitted and 100 mg per liter of i-inositol, 0.17 g per liter of $NaH_2PO_4 \cdot H_2O$ and varying amounts of steepwater were added.

Steepwater is available from CPC International Inc., Englewood Cliffs, N.J., as E801 ARGO ®Steepwater. The sample used had a pH of 4.6 and contained 52.5% dry solids. Analysis showed that on a dry solids basis it contained: total nitrogen, 8.7%; amino acids, 19.0%; lactic acid, 28.8%; total phosphate, 9.9%; phytic acid, 9.5%; ash, 18.6%; reducing sugars, 1.8%; and less than 10 parts per million (ppm) of heavy metals.

TABLE I

| SHOOT INITIATION MEDIUM | |
|---|---|
| Formulation | mg/l |
| $NH_4NO_3$ | 1,650 |
| $KNO_3$ | 1,900 |
| $CaCl_2.2H_2O$ | 440 |
| $MgSO_4.7H_2O$ | 370 |
| $KH_2PO_4$ | 170 |
| $Na_2EDTA$ | 37.3 |
| $FeSO_4.7H_2O$ | 27.8 |
| $H_3BO_3$ | 6.2 |
| $MnSO_4.H_2O$ | 16.9 |
| $ZnSO_4.7H_2O$ | 8.6 |
| KI | 0.83 |
| $Na_2MoO_4.2H_2O$ | 0.25 |
| $CuSO_4.5H_2O$ | 0.025 |
| $CoCl_2.6H_2O$ | 0.025 |
| Sucrose | 30,000 |
| Thiamine.HCl | 0.4 |
| Kinetin | 1.0 |
| Indoleacetic Acid | 1.0 |

Ten replicate tubes were each inoculated with a single shoot. Each tube (25×150 mm) contained 20 ml of medium which was adjusted to pH 6.0 and solidified with 1% agar. Sealed tubes were kept under 16 hr light at 250 ft-candles at a constant 25° C. Thirty days after inoculation the shoots were counted and recorded as the first subculture. The contents of each tube was cut into sections with each section containing a single shoot. These shoots were then transferred to fresh media. After an additional 30 days, the number of shoots was again counted and listed as the second subculture. The results are given in Table II.

The experiments were repeated except that the steepwater used was an ultrafiltration retentate prepared as follows. A dilute solution of commercial steepwater, filtered through a precoat filter, was processed through an ultrafiltration unit using a 1000-molecular weight cutoff membrane (Osmonics Sepa-O polysulfone) at a 9:1 permeate to retentate ratio. Operating pressure was 100 pounds per square inch at a temperature of about 10° C. The retentate was then evaporated under reduced pressure at 50°-60° C. to a concentration of 46.2% dry solids. Analysis of this material indicated that it contained on a dry solids basis 8.0% nitrogen; 13.4% lactic acid; 9.4% ash; and 0.8% reducing sugars. Results of these experiments are also given in Table II.

In control experiments, shoots were grown on nodal propagation media under the same conditions except that the media contained no steepwater. The results of these experiments, given in Table II, show that shoots grown on media containing steepwater produce a substantially larger number of new shoots than do the shoots grown on the medium without added steepwater. The results further show that the optimum level of steepwater solids in the medium is about 2.5 g per liter of medium.

TABLE II

EFFECT OF STEEPWATER ON RATE OF SHOOT DEVELOPMENT IN POTATO SHOOT CULTURES

| Steepwater in Medium (g/l) | Number of Shoots | |
|---|---|---|
| | First Subculture | Second Subculture |
| None (Control) | 79 | 546 |
| 0.05 | 89 | 644 |
| 0.5 | 91 | 773 |
| 2.5 | 113 | —[a] |
| 5.0 | 88 | 586 |
| 0.05 (Ultrafiltered) | 90 | 607 |
| 0.50 (Ultrafiltered) | 110 | 795 |
| 2.5 (Ultrafiltered) | 108 | 999 |
| 5.0 (Ultrafiltered) | 116 | 813 |

[a]Culture contaminated.

EXAMPLE 2

The process of Example 1 was repeated using medium prepared from a different batch of steepwater. The first subculture was grown for 4 weeks. The individual shoots were then separated and grown on fresh medium. At the end of an additional 4 weeks, the plants were harvested and the number of shoots and root tips were counted for each plant. The results given in Table III show that the plants produced from the shoots grown on a medium containing steepwater were more highly branched, producing more shoots than the plants grown on the same medium without steepwater. Furthermore, the plants grown on a medium containing steepwater had a highly branched and vigorous root system with multiple root tips.

TABLE III

EFFECT OF STEEPWATER ON RATE OF SHOOT AND ROOT TIP DEVELOPMENT IN POTATO SHOOT CULTURES

| Steepwater in Medium (g/l) | Number of Shoots[a] | Number of Root Tips[a] |
|---|---|---|
| None (Control) | 8 | 4 |
| 0.5 | 9 | 6 |
| 2.5 | 14 | 18 |
| 5.0 | 13 | 18 |

[a]Average values for at least 10 plants.

Thus, it is apparent that there has been provided, in accordance with the invention, an improved method for the propagation of plants by multiple shoot formation from tissue cultures that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What we claimed is:

1. A process for increasing the rate of shoot formation in plant tissue cultures comprising:
    culturing an organized plant cell system selected from the group consisting of buds, stem segments, shoot tips, and meristems on a growth medium for said organized cell system;
    wherein said growth medium comprises an amount of corn steepwater sufficient to increase the rate of shoot formation.

2. The process of claim 12 wherein the medium comprises from about 0.05 g to about 5 g of steepwater solids per liter of medium.

3. The process of claim 2 wherein the steepwater is first ultrafiltered before it is added to the medium.

4. The process of claim 2 wherein the plants are potato plants and the organized cell system is the shoot tip from the "eyes" of a potato tuber.

5. A process for the propagation of a potato plant which comprises:
   culturing shoots of the potato plant on nodal propagation media which comprises steepwater until the shoots produce multiple nodes;
   cutting the cultured material into sections, each of said sections containing a single node; and
   subculturing each section containing a single node on nodal propagation media which comprises steepwater to produce multiple copies of the potato plant.

6. The process of claim 5 wherein the medium comprises from about 0.05 g to about 5 g of steepwater solids per liter of medium.

7. The process of claim 6 wherein the medium comprises from about 0.5 g to about 5 g of steepwater solids per liter of medium.

8. The process of claim 6 wherein the steepwater is first ultrafiltered before it is added to the medium.

9. A process for the clonal propagation of potato plants which comprises the steps of:
   (1) excising shoot tips from "eyes" of a potato tuber from the potato plant;
   (2) placing the excised shoot tips on shoot initiating media;
   (3) culturing the shoot tips on the shoot initiating media until the shoot tips have produced multiple nodes;
   (4) cutting the shoots containing multiple nodes into separate shoots, each of which contains an individual node;
   (5) culturing the shoots containing individual nodes on nodal propagation media which comprises steepwater until the shoots have again produced multiple nodes;
   (6) cutting the subcultured material into sections, each of said sections containing a single node; and
   (7) subculturing each section containing a single node on nodal propagation media which comprises steepwater to produce multiple copies of the potato plant.

10. The process of claim 9 wherein the medium comprises from about 0.05 g to about 5 g of steepwater solids per liter of medium.

11. The process of claim 10 wherein the medium comprises from about 0.5 g to about 5 g of steepwater solids per liter of medium.

* * * * *